United States Patent
Lou et al.

(10) Patent No.: US 6,761,833 B2
(45) Date of Patent: Jul. 13, 2004

(54) STABILIZATION OF MONOMERS BY COMPOSITIONS BASED ON ALKYLHYDROXYLAMINES

(75) Inventors: Jianfeng Lou, Wayne, PA (US); Martin Nosowitz, Paoli, PA (US)

(73) Assignee: Atofina Chemicals, Inc., Philadelphia, PA (US)

( * ) Notice: Subject to any disclaimer, the term of this patent is extended or adjusted under 35 U.S.C. 154(b) by 136 days.

(21) Appl. No.: 10/066,923

(22) Filed: Feb. 4, 2002

(65) Prior Publication Data
US 2002/0190238 A1 Dec. 19, 2002

Related U.S. Application Data
(60) Provisional application No. 60/277,214, filed on Mar. 20, 2001.

(51) Int. Cl.⁷ ................................................ C09K 3/00
(52) U.S. Cl. .................. 252/182.29; 252/404; 252/405; 252/406; 585/4; 524/186
(58) Field of Search ...................... 252/182.29, 183.12, 252/405, 406, 182.11, 404; 585/4; 524/186

(56) References Cited

U.S. PATENT DOCUMENTS

| 3,878,181 A | | 4/1975 | Myer-Mader et al. |
| 4,409,408 A | | 10/1983 | Miller |
| 4,628,132 A | * | 12/1986 | Miller .......................... 585/4 |
| 4,654,450 A | | 3/1987 | Miller |
| 4,720,566 A | | 1/1988 | Martin |
| 4,956,020 A | | 9/1990 | Nakajima |
| 4,997,990 A | * | 3/1991 | Campbell et al. ............... 585/2 |
| 5,028,340 A | * | 7/1991 | Gallup ....................... 210/753 |
| 5,282,957 A | | 2/1994 | Wright et al. |
| 5,396,004 A | | 3/1995 | Arhancet et al. |
| 5,426,257 A | | 6/1995 | Arhancet |
| 5,446,220 A | | 8/1995 | Arhancet |
| 5,510,547 A | | 4/1996 | Arhancet et al. |
| 6,284,936 B2 | * | 9/2001 | Shahid .......................... 585/4 |
| 6,495,065 B1 | * | 12/2002 | Lou et al. .............. 252/183.12 |

FOREIGN PATENT DOCUMENTS

| AT | RD406010 | * | 2/1998 |
| CA | 1227449 | | 9/1987 |
| JP | 357165332 | * | 10/1982 |
| JP | 01013041 | | 1/1989 |
| JP | 64013041 | * | 1/1989 |
| JP | 06345832 | * | 12/1994 |
| JP | 410147603 | * | 6/1998 |
| JP | 10-251663 | | 9/1998 |
| JP | 63-223003 | | 9/1998 |
| WO | WO 96/38399 | | 12/1996 |
| WO | WO 96/41783 | | 12/1996 |
| WO | WO 97/35821 | | 10/1997 |
| WO | WO 98/02403 | | 1/1998 |

* cited by examiner

Primary Examiner—Cephia D. Toomer
(74) Attorney, Agent, or Firm—Gilbert W. Rudman

(57) ABSTRACT

Vinyl monomers are stabilized by a composition which includes an alkyl hydroxyl amine and a sulfide compound or at least two alkyl hydroxyl amines and a phenolic compound.

8 Claims, No Drawings

STABILIZATION OF MONOMERS BY COMPOSITIONS BASED ON ALKYLHYDROXYLAMINES

REFERENCE TO RELATED APPLICATION

This application claims the benefit of U.S. Provisional Application Serial No. 60/277,214, filed Mar. 20, 2001.

FIELD OF THE INVENTION

This invention relates to compositions for stabilization of vinyl monomers; the compositions include (A) at least one alkyl hydroxyl amine compound and at least one sulfide compound, or (B) at least two alkyl hydroxyl amine compounds and at least one phenolic compound.

BACKGROUND OF THE INVENTION

During the manufacture, storage, and transportation of vinyl monomers, undesired polymers or organic peroxides are often formed.

During manufacture, undesired polymers or organic peroxides foul the processing equipment which cause reduced heat transfer and increased downtime cleaning.

During storage and transportation, these unwanted polymers or organic peroxides not only affect the product quality but also present an explosion hazard. Butadiene, for example, forms butadiene peroxide in contact with oxygen which can lead to uncontrolled polymerization.

Currently, various phenolic compounds are used to stabilize vinyl monomers, but they are toxic, expensive, and not effective inhibiting popcorns in vapor phase. For certain applications, these phenolic stabilizers require the presence of oxygen for proper functioning as in the case of styrene stabilization using 4-tert-butylcatechol (TBC).

Also, the prior art discloses the use of individual dialkylhydroxylamines and alkylhydroxylamine-based composites as stabilizers for vinyl monomers.

Synergistic effects have been claimed for composite stabilizers of alkylhydroxylamines with water-soluble amines, trialkylamine oxides, phenylenediamines, oximes, alkyl benzene sulfonic acids, dinitrophenols, TBC, and benzoquinone deriatives. However, the previously disclosed composites either focus on two-component stabilizing systems or are limited to only one type of vinyl monomers under restricted conditions.

Examples of the prior art follow.

Mayer-Mader, R.; Hohmann, G; U.S. Pat. No. 3,878,181; 1975; (Bayer Aktiengesellschaft) discloses a process for terminating emulsion polymerization of chloroprene and/or 2,3-dichlorobutadiene using a mixture of DEHA and a water-soluble amine (such as triethanolamine).

Miller, R. F.; U.S. Pat. No. 4,409,408; 1983; (Atlantic Richfield Company) discloses a mixture of N,N-dialkylhydroxylamine and teriary alkylcatechol for stabilizing vinyl aromatic monomers. Specific claims are made for the synergistic effect of a DEHA/TBC mixture in stabilizing styrene or alkyl substituted styrene.

Link, J.; Miller, R. F.; CA Patent 1,227,449; 1987; (Atlantic Richfield Company) discloses a method of using lower dialkylhydroxylamines to inhibit polymerization of hydrocarbons during their processing. Specific claims are made for butadiene where DEHA and a blend of DEHA and DEHA exhibited high performance.

Miller, R. F.; U.S. Pat. No. 4,654,450; 1987; (Atlantic Richfield Company) describes the use of a mixture of a N,N-dialkylhydroxylamine and an alkyl benzene sulfonic acid to stabilize vinyl aromatic compounds. Specific claims are made for DEHA-based composite stabilizer.

Martin, J. F.; U.S. Pat. No. 4,720,566; 1988; (Betz Laboratories, Inc.) describes the use of a mixture of a hydroxylamine and a phenylenediamine compound to inhibit polymerization of acrylonitrile, particularly in a quench column.

Sato, K.; Nishii, K.; Ito, H.; JP Patent # 63,223,003; 1988 (Tokai Electro-Chemical Co., Ltd.) discloses the use of a mixture of trialkylamine oxides and N,N-diakylhydroxylamines to inhibit popcorn formation in an olefin recovery or purification system.

Nakajima, S.; JP Patent # 01,013,041; 1989; (Hakuto Chemical Co., Ltd.) describes a composition for inhibiting popcorn formation in olefin production apparatus. The disclosed composition comprises compounds selected from hydroxylamines, oximes, mercaptans, etc., and optionally antioxidants and surfactants.

Nakajima, S.; U.S. Pat. No. 4,956,020; 1990; (Hakuto Chemical Co., Ltd.) discloses an inhibitor for preventing popcorn polymer growth on the inner surface of an olefin production unit. Such an inhibitor comprises at least one compound selected from a group that include phenylenediamine, hydroxylamine, etc. The inhibitor is applied to the inner surface when the operation of the production apparatus is suspended.

Wright, B. E.; Weaver, C. E.; Reid, D. K.; U.S. Pat. No. 5,282,957; 1994; (Betz Laboratories, Inc.) claims a method of using a hydroxyakylhydroxylamine compound to inhibit polymerization of hydrocarbons during their processing and storage.

Arhancet, G. B.; Henrici, I. K.; U.S. Pat. No. 5,396,004; 1995; (Betz Laboratories, Inc.) discloses a mixture of phenylenediamine and a hydroxylamine compound for inhibiting polymerization of vinyl aromatic monomers under distillation conditions.

Arhancet, G. B.; U.S. Pat. No. 5,426,257; 1995; (Betz Laboratories, Inc.) discloses the use of a hydroxylamine-based composition for inhibiting polymerization of vinyl aromatic monomers in the absence of oxygen. Such a composition is either a mixture of an oxime and a hydroxylamine compound, or a mixture of an oxime, a hydroxylamine, and a phenylenediamine compound.

Arhancet, G. B.; U.S. Pat. No. 5,446,220; 1995; (Betz Laboratories, Inc.) discloses the use of a hydroxylamine-based ternary composition for inhibiting polymerization of vinyl aromatic monomers in oxygen-free processing systems. Such a composition comprises a dinitrophenol, a hydroxylamine, and a phenylenediamine compound. The preferred hydroxylamine compound is claimed to be bishydroxypropylhydroxylamine.

Arhancet, G. B.; Henrici, I. K.; U.S. Pat. No. 5,510,547; 1996; (Betz Laboratories, Inc.) discloses the use of a mixture of a hydroxylamine and a phenylenediamine compound to inhibit polymerization of vinyl aromatic monomers in oxygen-free processing systems. Specifically claimed hydroxylamines are DEHA and isopropylhydroxylamine (NiPHA).

Arhancet, G. B.; Henrici, I. K.; WO Patent # 9,641,783; 1996; (Betz Laboratories, Inc.) discloses a method of inhibiting polymerization of vinyl aromatic monomers using a mixture of a hydroxylamine compound and a benzoquinone derivative. The preferred hydroxylamine in such a composition is bis(hydroxypropyl)hydroxylamine.

Arhancet, G. B.; Henrici, I. K.; Martin, J. F.; WO Patent # 9,638,399; 1996; (Betz Laboratories, Inc.) describes the use of a mixture of hydroxylamine compound and a dinitrosalicylic acid derivative to inhibit polymerization of vinyl aromatic monomers during processing. The preferred hydroxylamine in such a composition is bis(hydroxypropyl) hydroxylamine.

Arhancet, G. B.; Henrici, I. K.; WO Patent # 9,735,821; 1997; (BetzDearborn Inc.) discloses a composition for inhibiting polymerization of vinyl aromatic monomers in the absence of oxygen. Such a composition comprises a hydroxylamine and a phenylenediamine compound. Specifically claimed hydroxylamines are DEHA, NiPHA, and bis(hydroxypropyl)hydroxylamine.

Ukita, K.; Onodera, Y.; Futamura, S.; JP Patent # 10,251,663; 1998; (Nippon Zeon Co., Ltd.) discloses a method of preventing polymerization in an extractive distillation process for isoprene separation. In such a method, a di-lower-alkylhydroxylamine (e.g., DEHA) is added to the distillation column above the feeding point of the extraction solvent.

Arhancet, G. B.; Bringol, E. H.; WO Patent # 9,802,403; 1998; (BetzDearborn Inc.) provides a method of using a combination of a phenol and a hydroxylamine compound to inhibit polymerization of vinyl aromatic monomers in reactor effluent condenser and vent gas compressor systems. The most preferred hydroxylamine claimed is DEHA.

The objective of the present invention to develop improved stabilizing compositions compared to conventional phenolic stabilizers and alkylhydrooxyyl amine compositions.

SUMMARY OF THE INVENTION

The present invention relates to the synergistic behavior involving certain combinations of dialkylhydroxylamines with phenolic and sulfide compounds.

Compositions of the present invention are blends of alkylhydroxylamines with either phenolic compounds or sulfide compounds which are synergistic and superior to individual dialkylhydroxylamines and conventional stabilizers (such as TBC) based on their stabilizing ability.

Additional advantages for the compositions of the present invention include vapor-phase popcorn inhibition, low cost and toxicity, and scavenging of potentially present organic peroxides.

DETAILED DESCRIPTION OF THE INVENTION

Improved compositions have been developed for stabilizing vinyl monomers during their processing, storage, and shipping.

Such compositions are based on blends of two or more alkylhydroxylamines with phenolic antioxidants or blends of alkylhydroxylamines with sulfide compounds where synergistic effects are exploited for targeted applications.

Such stabilizing systems exhibited markedly superior performance to previously disclosed compositions and currently used commercial stabilizers.

In the composite system, the amine-based ingredients may vary between 10–90 wt. % of the total stabilizer. If an amine mixture is used, each amine compound may account for 20–80 wt. % of amines.

Such composite stabilizers find applications in stabilizing dienes (such as butadiene and isoprene), vinyl aromatic monomers (styrene and its derivatives), and acrylic acid and its esters.

An amine compound useful in the present invention may be an alkylhydroxylamine or its corresponding amine oxide.

The alkylhydroxylamine compound has the general formula:

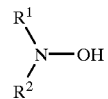

where $R^1$ and $R^2$ are the same or different, and they could be hydrogen, alkyl, hydroxyalkyl, alkoxyalkyl, and sulfonated alkyl groups, they could be cyclic or branched, but they may not both be H, a H and a methyl, and both be methyl.

Phenolic compounds useful in the present invention have the general formula:

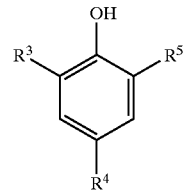

wherein $R^3$ and $R^5$ are the same or different, and can be hydrogen, alkyl, hydroxyl, and alkaryl groups; $R_4$ is $C_1$–$C_{20}$ alkyl, alkanoic acid ester, alkaryl, alkylamino, or amine groups.

The sulfide compound has the general formula:

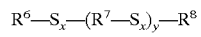

$$R^6-S_x-(R^7-S_x)_y-R^8$$

wherein each x is independently a number between 1–10, y is a number between 0–50, and $R^6$, $R^7$ and $R^8$ are the same or different, and can be alkyl and aryl groups. The aryl group is preferred to be phenolic.

A preferred sulfide is an alkyl phenol sulfide having the formula

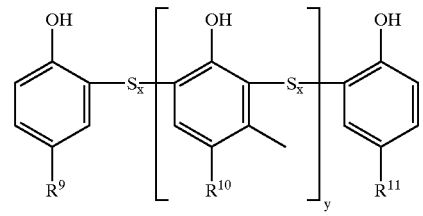

wherein each x is independently a number between 1–10, y is a number between 1–50, preferably 1–20, and $R^9$, $R^{10}$ are each 1,1-dimethylpropyl. A series of sulfides having such a formula are sold by ATOFINA Chemicals, Inc. under the trademark Vultac®.

In terms of the targeted applications of such compositions, the monomer being stabilized could be extended to other compounds of the same class based on their structural similarity and chemical reactivity.

Furthermore, the conditions for proper functioning of the disclosed stabilizers could be changed, and they include temperature, pressure, atmospheric and chemical environment. A chemical environment here refers to a solvent reservoir where targeted vinyl monomers are dissolved/dispersed. These speculations are based on theory, analogy, and limited experiments.

The composite stabilizers disclosed in this invention can be altered in that their composition could be varied, and various amine, phenolic and sulfide compounds could be used.

Typical synergistic compositions disclosed in this invention include two-component systems with at least one component being an alkylhydroxylamine (or its corresponding amine oxide), and three-component systems with two components being alkylhydroxylamines (or their corresponding amine oxides).

These compositions exhibit better performance inhibiting polymerization than currently used commercial stabilizers; they are suitable for stabilizing dienes (such as butadiene and isoprene), vinyl aromatic compounds (such as styrene and its derivatives), and acrylic acid and its esters.

The developed compositions are particularly advantageous for use under hostile environments, for example, chemical processing involving vinyl compounds at high temperatures. One such application is targeted at the process of extractive distillation involved in the manufacturing of butadiene and isoprene. Another such application is targeted at the process of manufacturing styrene from ethyl benzene dehydrogenation. In general, advantages of the disclosed compositions over conventional stabilizers include higher performance, lower toxicity and cost, and more effective vapor-phase popcorn inhibition. One example of such compositions is a binary stabilizer of diethylhydroxylamine (DEHA) and Vultac®, a series of alkyl phenol sulfides sold by ATOFINA Chemicals, Inc.; the composite shows excellent performance stabilizing styrene and its derivatives. Another example is a ternary stabilizer of DEHA, dibutylhydroxylamine (DBHA), and 4-tert-butylcatechol (TBC); this composite system exhibits superb performance stabilizing butadiene and isoprene at elevated temperatures.

The preferred monomer stabilizer among the disclosed compositions varies depending on targeted applications. In general, binary and ternary stabilizers are disclosed with at least one component being an alkylhydroxylamine. A binary DEHA/Vultac® system and a ternary DEHA/DBHA/TBC system, for example, appear to be advantageous over conventionally used TBC and other composite compositions in stabilizing divinylbenzene and butadiene, respectively.

In the binary system, alkylhydroxylamine is 10–90 wt. %, preferably, 40–80 wt. % of the total composition. The preferred alkylhydroxylamine is DEHA, and the preferred sulfide is an alkyl phenol sulfide, such as those sold under the trademark Vultac®.

In the ternary system, two alkylhydroxylamines account for 20–90%, preferably, 50–80% of the total composition; each hydroxylamine is 10–90 wt. %, preferably, 30–70 wt. % of hydroxylamines. The preferred alkylhydroxylamines are DEHA and DBHA, and the preferred phenolic compound is TBC.

The amount of stabilizer composition needed to effectively stabilize vinyl compounds depends on the type of monomer and the process conditions associated with particular applications. Generally, a level of 1–5000 ppm, and preferably 10–1000 ppm stabilizer is added to effectively prevent polymerization. These compositions could be added to the process streams during monomer manufacturing, or directly added to monomers during storage and shipping.

While the following examples illustrate the use of various materials in embodiments of the invention, it should be clear that there is no intention of so limiting the scope of the invention. On the contrary, it is intended that the breadth of the invention illustrated by reference to the following examples will apply to other embodiments that would be obvious to those skilled in the art.

EXAMPLE 1

Stabilization of Butadiene Under $N_2$

A heat-induced gum test was performed to evaluate various inhibitors for their ability to stabilize butadiene; the test is an adaption of ASTM D 381, "Standard Test Method for Existent Gum in Fuels by Jet Evaporation", and ASTM D 873, "Standard Test Method for Oxidation Stability of Aviation Fuels (Potential Residue Method)".

In a typical experiment, a 100 ppm inhibitor was added to butadiene to prepare a 100 mL test mixture, and the mixture was maintained at 100° C. and under 100 psig $N_2$ for 24 hrs in a heat-aging bomb. Various stabilizers based on DEHA, DBHA, and TBC have been evaluated, and the results of these tests are presented in Table 1.

The results indicate that a ternary stabilizer of 35 ppm DEHA, 35 ppm DBHA, and 30 ppm TBC is the most effective among the investigated stabilizers. This ternary system produced 234 mg/100 mL of insoluble gum and 460 mg/100 mL of total gum, a ~40% reduction in insoluble gum and a ~20% reduction in total gum compared to the best of the rest inhibitors in each category.

TABLE 1

| Stabilizer | Soluble Gum | Insoluble Gum | Total Gum |
| --- | --- | --- | --- |
| 100 ppm TBC[b] | 87 mg/100 mL | 549 mg/100 mL | 636 mg/100 mL |
| 100 ppm DEHA | 383 mg/100 mL | 345 mg/100 mL | 728 mg/100 mL |
| 100 ppm DBHA | 316 mg/100 mL | 602 mg/100 mL | 918 mg/100 mL |
| 50 ppm DEHA/ 50 ppm DBHA | 318 mg/100 mL | 796 mg/100 mL | 1114 mg/100 mL |
| 50 ppm DEHA/ 50 ppm TBC[b] | 189 mg/100 mL | 382 mg/100 mL | 571 mg/100 mL |
| 50 ppm TBC/ 50 ppm DBHA | 210 mg/100 mL | 899 mg/100 mL | 1109 mg/100 mL |
| 30 ppm TBC/ 35 ppm DEHA/ 35 ppm DBHA[b] | 226 mg/100 mL | 234 mg/100 mL | 460 mg/100 mL |

[a]Experimental conditions: 100° C., 24 hrs, under 100 psig $N_2$ (min. 99.6% purity). Test results are expressed in mg gum per 100 mL of butadiene. The insoluble gum refers to material sticking to reactor lines that is not removed by butadiene and heptane, and the soluble gum is the residual stuff after butadiene is evaporated (under $N_2$, at ~162° C., for 0.5 hr).
[b]The result is an average of two duplicate runs.

EXAMPLE 2

Stabilization of Divinylbenzene

Solution polymerization of divinylbenzene was performed where the amount of polymer was measured with time in the presence of various inhibitors.

In a typical experiment, uninhibited divinylbenzene and toluene (3:1 weight ratio) were mixed at room temperature, and 1000 ppm of stabilizer (based on the weight of divinylbenzene) was added to the resulting mixture. Such mixture (50 mL) was then charged to a 100 mL round bottom flask that was equilibrated at 100° C. and thoroughly purged of air by nitrogen gas. Samples were drawn from the flask periodically, and the amount of polymer formed was monitored by weight analysis.

Various stabilizers based on DEHA, TBC and Vultac® 7 (an amylphenol disulfide polymer) have been tested for their performance as divinylbenzene stabilizer; Table 2 lists the results for these experiments. The results indicate that the DEHA/TBC and DEHA/Vultac® 7 binary systems exhibit the best performance among the investigated stabilizers as divinylbenzene stabilizer. In Table 2, the widely used TBC inhibitor results in 6.66% conversion of divinylbenzene to polymer after 1.0 hr at 100° C.; the previously disclosed DEHA/TBC blend leads to 2.44% conversion after 1 hr; the composition of the invention, DEHA/Vultac® 7 blend, results in 2.04% conversion after 1 hr. Thus, the DEHA/Vultac®7 composition, as does the DETA/TBC composition, exhibits markedly better performance stabilizing divinylbenzene than does the conventional TBC stabilizer.

TABLE 2[a]

| Stabilizer | Time, hr. | | | | | |
|---|---|---|---|---|---|---|
| | 0.25 | 0.50 | 0.75 | 1.0 | 1.5 | 2 |
| | Weight % of divinylbenzene converted to polymer | | | | | |
| None | 1.43 | 5.39 | — | — | — | — |
| 1000 ppm TBC | 0.36 | 2.06 | 3.90 | 6.66 | — | — |
| 1000 ppm DEHA | 0.20 | 0.43 | 1.88 | 2.73 | 4.88 | 7.25 |
| 1000 ppm Vultac ® 7 | 0.75 | 2.29 | 4.03 | 6.04 | — | — |
| 500 ppm TBC/ 500 ppm Vultac ® 7 | 0.39 | 1.86 | 4.29 | 5.53 | — | — |
| 500 ppm DEHA/ 500 ppm TBC[b] | 0.07 | 0.76 | 1.46 | 2.44 | 4.13 | 5.95 |
| 500 ppm DEHA/ 500 ppm Vultac ® 7[b] | 0.05 | 0.58 | 1.53 | 2.09 | 4.10 | 6.20 |

[a]Experimental conditions: 100° C., under $N_2$ (50 cm$^3$/min);
[b]The results were averaged from two duplicate runs.

While specific embodiments have been described herein, it should be apparent to those skilled in the art that various modifications thereof can be made without departing from the true spirit and scope of the invention. Accordingly, it is intended that the following claims cover all such modifications within the full inventive concept.

What is claimed is:

1. A composition for stabilization of vinyl monomers; the composition including (a) at least one alkyl hydroxyl amine compound and at least one phenolic sulfide compound.

2. The composition of claim 1 wherein amine components are 10–90 wt. % of the total composition.

3. A process for the stabilization of dienes, vinyl aromatic monomers, or acrylic acid and its esters by the addition of the composition of claim 1.

4. The composition of claim 1 wherein each of the alkylhydroxylamine compounds has the general formula:

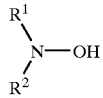

where $R^1$ and $R^2$ are the same or different, and can be hydrogen, alkyl, hydroxyalkyl, alkoxyalkyl, and sulfonated alkyl groups, cyclic or branched, but cannot both be H, a H and a methyl, or both be methyl.

5. The composition of claim 1 wherein the phenolic sulfide compound has the general formula:

$$R^6-S_x-(R^7-S_x)_y-R^8$$

wherein each x is independently a number between 1–10, y is a number between 0–50 and $R^6$, $R^7$ and $R^8$ are the same or different, and can be alkyl and aryl groups.

6. The composition of claim 5 wherein the sulfide is an alkyl phenol sulfide having the formula:

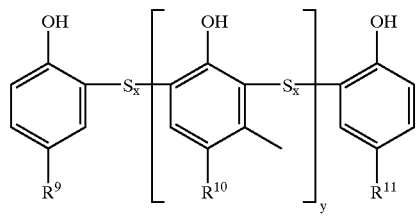

wherein each x is independently a number between 1–10 y is a number between 1–50 and $R^9$, $R^{10}$ and $R^{11}$ are each 1,1-dimethylpropyl.

7. The composition of claim 6 wherein the sulfide is a an amylphenoldisulfide polymer.

8. The composition of claim 1 used to stabilize butadiene, isoprene or styrene.

* * * * *